United States Patent
Goebel et al.

(10) Patent No.: US 6,479,815 B1
(45) Date of Patent: Nov. 12, 2002

(54) ION MOBILITY SPECTROMETER

(75) Inventors: Johann Goebel, Munich (DE); Christoph Wagner, Munich (DE); Ulrich Breit, Munich (DE); Harald Ertl, Geretsried (DE)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 09/647,991
(22) PCT Filed: Apr. 1, 1999
(86) PCT No.: PCT/DE99/00993
§ 371 (c)(1), (2), (4) Date: Oct. 10, 2000
(87) PCT Pub. No.: WO99/51979
PCT Pub. Date: Oct. 14, 1999

(30) Foreign Application Priority Data

Apr. 7, 1998 (DE) .......................................... 198 15 436

(51) Int. Cl.$^7$ ................................................ H01J 49/40
(52) U.S. Cl. .................. 250/287; 250/287; 250/290; 250/286; 250/288
(58) Field of Search ................................. 250/287, 282, 250/290, 286, 288, 294, 309, 281

(56) References Cited

U.S. PATENT DOCUMENTS

| 3,596,088 | A |   | 7/1971 | Cohen et al. | ......... 250/41.9 TF |
| 4,855,595 | A |   | 8/1989 | Blanchard | .................... 250/287 |
| 5,235,182 | A |   | 8/1993 | Avida et al. | ................. 250/286 |
| 5,420,424 | A |   | 5/1995 | Carnhan et al. | ............. 250/287 |
| 5,455,417 | A | * | 10/1995 | Sacristan | ..................... 250/282 |
| 5,965,882 | A | * | 10/1999 | Megerle et al. | .............. 250/287 |

FOREIGN PATENT DOCUMENTS

| CA | 2222847 | * | 6/1998 |
| DE | 41 34 212 A2 |   | 4/1993 |
| DE | 195 13 459 A1 |   | 1/1996 |
| DE | 196 50 612 A1 |   | 6/1998 |
| EP | 0 253 155 A1 |   | 11/1988 |
| WO | WO 98/08087 |   | 2/1998 |

* cited by examiner

Primary Examiner—John R. Lee
Assistant Examiner—Kalimah Fernandez
(74) Attorney, Agent, or Firm—Crowell & Moring LLP

(57) ABSTRACT

An ion mobility spectrometer has two opposing wall elements connected by at least one spacer with parallel, mutually assigned, planar, gas-guiding wall surfaces with opposing conductor structures to generate a drift field. The ratio of distance of the gas-guiding wall surfaces to the field-generating width of the conductor structure perpendicular to the drift direction is less than 1:2 and is advantageously 1:3 to 1:10.

10 Claims, 1 Drawing Sheet

ION MOBILITY SPECTROMETER

BACKGROUND AND SUMMARY OF THE INVENTION

This application claims the priority of PCT International Application No. PCT/DE99/00993, filed Apr. 1, 1999, and German patent document 198 15 436.4, filed Apr. 1, 1999, the disclosure of which is expressly incorporated by reference herein.

The invention concerns an ion mobility spectrometer (IMS) of the type having an ionization area for ionizing a substance which is to be analyzed, forming a gaseous ion mixture, at least one ion gate neighboring the ionization area, which gate can be electrically switched between a blocked and an open state, a drift area neighboring the ion gate with an electrical drift field running along a drift path, and an ion collector that is connected to electronics to detect contacting ions.

German patent document DE 41 34 212 A1 discloses an IMS that is miniaturized by the monolithic integration of the ion source, the drift path, the collector electrodes and the required electronics, based on a semiconductor material. A concrete design of such a device that can be efficiently created, especially by means of semiconductor technology is, however, not disclosed.

In German patent document DE 196 50 612, the ion gate, the drift chamber and the ion collector of an IMS are constructed of pieces that can be cut out of conventional semiconductor materials. In particular, the ion gate is designed as a grid perpendicular to the drift direction that is comparatively involved to manufacturer using semiconductor technology. Connecting the ionization and drift chamber via the ion gate requires a substantial amount of mechanical processing.

One object of the present invention is to provide a miniaturizable IMS that is easier to design and manufacture than earlier versions.

This and other objects and advantages are achieved by the IMS according to the invention, which is based on the recognition that the previous three-dimensional gas guidance in the ionization and drift area utilized by prior art devices can be reduced to an essentially two-dimensional design. When there is a sufficiently small distance between two parallel, gas-delimiting wall surfaces, a side seal is not necessary so that one or more simple spacers are sufficient to connect the wall elements, which are pressed against the spacers via clamps, etc. With such a planar arrangement, the ion gate can be formed by planar conductor structures on the wall elements, which substantially reduces the manufacturing effort, especially since special chambers for ionization and the drift path are no longer necessary. The ion collector can also be manufactured in the same way, which represents a substantial simplification.

Given the planar design of the wall elements and conductor structures, conductive rubber contacts can be used to contact the conductive strips that are familiar from LCD technology, where they are used to contact reliably a large number of adjacent contact surfaces.

Other objects, advantages and novel features of the present invention will become apparent from the following detailed description of the invention when considered in conjunction with the accompanying drawings.

BRIEF DESCRIPTION OF THE DRAWINGS

FIG. 1.*b* is a graph which shows a potential characteristic of the conductor strips in FIG. 1.*a*.

DETAILED DESCRIPTION OF THE DRAWINGS

Figure 1A:
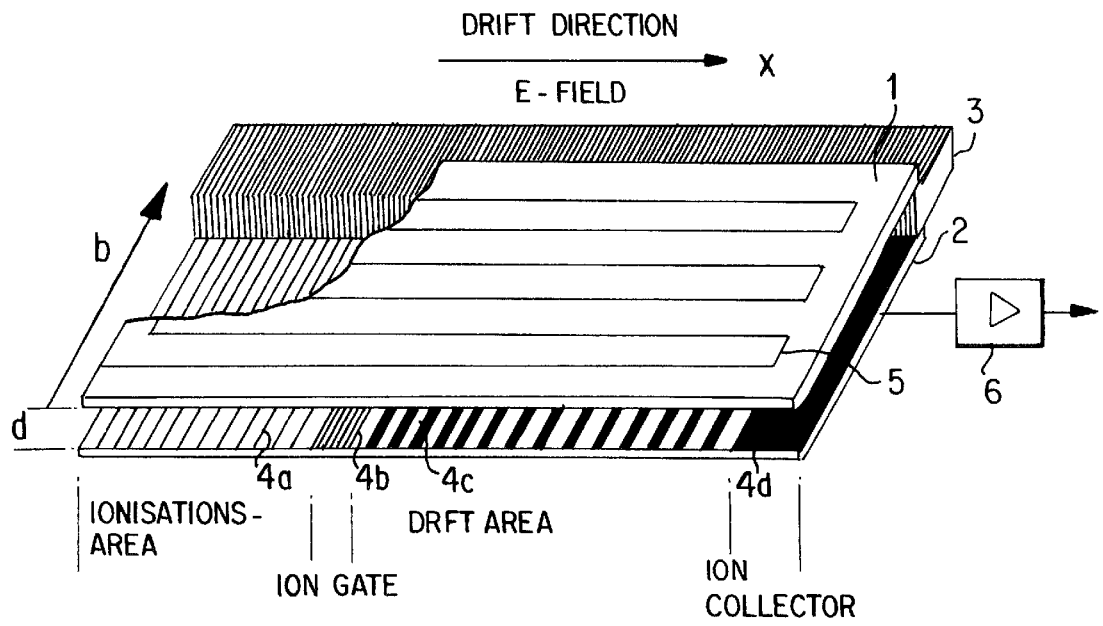
FIG. 1.*a* shows a schematic perspective view of an exemplary embodiment of an IMS according to the invention.
Figure 1B:
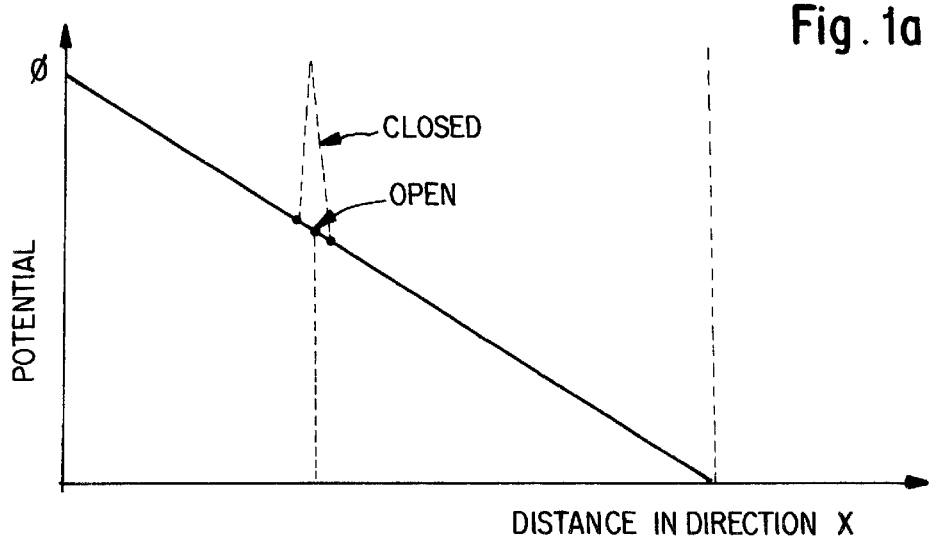

The IMS in FIG. 1.*a* essentially has two adjacent parallel planar plates 1 and 2 consisting of, for example, glass, ceramic, or a semiconductor material. These plates are spaced apart at a distance d, which is maintained by spacers (not shown) in the form of blocks or strips clamped between the plates 1 and 2. The plates form a gas-conducting channel having a width b (possibly including the bordering spacers or contact elements 3 described further below), which is at least twice (advantageously five to ten times) the distance d. The respective insides of the plates 1 and 2 have conductor structures 4 that serve to generate an electrical field E in the lengthwise direction (X direction) in the gap between the two plates 1 and 2. The conductor structures consist of conductor strips perpendicular to the X direction that are electrically connected via a thin resistance layer (not shown) or individual resistors. One end of the conductor strips can also be alternatingly connected to the left neighboring strip, and the other end can be connected to the right neighboring strip to form a continuous, meandering conductor. In the figure, the conductor strips have different thicknesses and are spaced differently to illustrate different areas. This can be useful, but it is not necessary. In the simplest case, an equal spacing of the conductor strips of approximately 200_m is sufficient. The individual conductor strips are contacted at one side via a comb-like, segmented conductive rubber strip 3 so that different potentials—can be applied to generate the drift field, control the ion gate, and for the ion collector.

The left part of the area 4*a* enclosed by the plates serves to supply the drift gas and the sample material, and it also serves as an ionization area. Simple and efficient ionization can achieved e.g., by a radioactive Ni 63 source that either is at the sides or in the flow area extending in the X direction.

The ion gate is substantially simplified by the planar arrangement. A part of the conductor strip, electrically insulated from the other conductor strips in the area of the conductor structure 4, is designated as the ion gate 4*b*. While the potential characteristic of the conductor strips (FIG. 1.*b*) decreases with a settable gradient from left to right when the ion gate is open, the continuity of the potential characteristic can be interrupted in a triangular shape to close the ion gate at the provided conductor strips so that the ions in the ionization area cannot pass through the potential barrier.

The ion collection 4*d* formed by conductor layers on the inner walls of the plates 1 and 2 like the ion gate is connected to an electronics unit 6 for detecting contacting ions or electrons.

With the above-described construction, the ionization area 4*a*, the ion gate 4*b*, the drift area 4*c* and the ion collection 4*d* form a continuous channel whose flow is not disturbed, and whose end faces can easily be connected to corresponding'sources for the drift or sample gas.

Another advantage of the planar design is that other components can be on the surfaces of the plates 1 and 2. For example, it is possible to place a heater in the form of a conductor loop 5 on the surfaces to electrically heat the ionization and drift area. The advantage of such a heater is that the reaction kinetics can be improved in the formation of ions within the ionization area. In the drift area, the heater counteracts so-called "poisoning" from ions deposited on the walls.

The components and structures described above can be loft manufactured using simple standard processes from microsystem technology, with great precision, and allowing numerous possible variations. This also allows mass production at a reasonable price.

An essential advantage of the planar design is that it is substantially easier to shape and guide the field, especially in the drift area. Hence, correspondingly curved conductor strips can be applied to the flat inner surfaces of plates 1 and 2 instead of the straight conductor strips to achieve effects familiar from electron optics such as a focusing the ion stream. In this manner, ions can be prevented from drifting out of any open side areas.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An ion mobility spectrometer comprising:
   an ionization area for ionizing a substance which is to be analyzed, and forming a gaseous ion mixture;
   at least one ion gate adjacent the ionization area which gate can be electrically switched between a blocked and open state;
   a drift area neighboring the ion gate with an electrical drift field that is generated by conductor structures that are perpendicular to the drift path; and
   an ion collector that is connected to an electronics unit to detect contacting ions or electrons; wherein
      at least one of the ionization area and the drift area comprises opposing wall elements connected by at least one spacer, which wall elements have parallel, substantially planar opposing wall surfaces that delimit the gaseous ion mixture; and
      the ratio of distance between said wall surfaces that delimit the gaseous ion mixture to a field-generating width of the conductor structures perpendicular to a drift direction is less than 1:2.

2. The ion mobility spectrometer according to claim 1, wherein the ratio of the distance between the wall surfaces that delimit the gaseous ion mixture to the field-generating width of the conductor structures perpendicular to the drift direction is between 1:3 and 1:10.

3. The ion mobility spectrometer according to claim 1, wherein the ratio of the distance between the wall surfaces that delimit the gaseous ion mixture to the field-generating width of the conductor structures perpendicular to the drift direction is between 1:5 and 1:10.

4. The ion mobility spectrometer according to claim 1, wherein at least one of the ion gate and the ion collector is formed by separate areas of the conductor structure that can be electrically controlled separately.

5. The ion mobility spectrometer according to claim 1, wherein the conductor structures have parallel conductor strips that are adjacent to each other in the drift direction and are alternatingly connected at the respective ends.

6. The ion mobility spectrometer according to claim 5, wherein the conductor strips are curved.

7. The ion mobility spectrometer according to claim 1, wherein at least some of the conductor strips are separate from each other and connected to each other with a resistance layer.

8. The ion mobility spectrometer according to claim 1, wherein at least one wall element in one of the ionization area and the drift area has a heater that is electrically insulated from the conductor structure.

9. The ion mobility spectrometer according to claim 6, wherein the conductor strips of at least one of the conductor structures and the heater have a sectioned conductive rubber contact at least at one end.

10. The ion mobility spectrometer according to claim 1, wherein the conductor structures extend over the ionization and drift area, said ion mobility spectrometer further comprising:
    means for generating an additional drift field in the ionization area; and
    means for generating a potential barrier in the area of the ion gate.

* * * * *